United States Patent
Ingram et al.

(10) Patent No.: US 10,018,570 B2
(45) Date of Patent: Jul. 10, 2018

(54) COMBINED SURFACE INSPECTION USING MULTIPLE SCANNERS

(71) Applicant: The Boeing Company, Chicago, IL (US)

(72) Inventors: Luke C. Ingram, Summerville, SC (US); Anthony W. Baker, Gilbertsville, PA (US); Steven A. Dorris, Saint Peters, MO (US); Christopher P. Bellavia, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/347,281

(22) Filed: Nov. 9, 2016

(65) Prior Publication Data
US 2018/0128751 A1     May 10, 2018

(51) Int. Cl.
*G01N 21/00* (2006.01)
*G01N 21/88* (2006.01)

(52) U.S. Cl.
CPC ... *G01N 21/8851* (2013.01); *G01N 2201/061* (2013.01)

(58) Field of Classification Search
CPC ......... G01N 21/8851; G01N 2201/061; H04N 7/18; H04N 5/23238; B61L 23/04; B01B 11/25
See application file for complete search history.

(56) References Cited

U.S. PATENT DOCUMENTS

| 5,383,135 A | 1/1995 | Shofner et al. | |
|---|---|---|---|
| 2001/0040624 A1* | 11/2001 | Kobayashi | H04N 5/23238 348/152 |
| 2004/0247170 A1 | 12/2004 | Furze et al. | |
| 2015/0042788 A1 | 2/2015 | Fujiwara | |
| 2016/0207551 A1* | 7/2016 | Mesher | B61L 23/04 |

OTHER PUBLICATIONS

"UltraHigh Speed Inline Profilometer: LJV series", Keyence Corporation, Retrieved from the Internet: http://www.keyence.com/products/measure/laser-2d/lj-v/models/lj-v7200/index.jsp,, 2016, 2 pgs.

"European Application Serial No. 17191926.9, Search Report dated Mar. 9, 2018", 7 pgs.

* cited by examiner

*Primary Examiner* — Jamil Ahmed
(74) *Attorney, Agent, or Firm* — Kwan & Olynick LLP

(57) ABSTRACT

Provided are methods and systems for inspecting surfaces of various components, such as evaluating height deviations on these surfaces. A method involves aggregating inspection data from multiple line scanners into a combined data set. This combined data set represents a portion of the surface that is larger than the field of measurement any one of the scanners. Furthermore, each pair of adjacent scanners operate at different periods of time to avoid interference. Because operating periods are offset, surface portions scanned by the pair of adjacent scanners can overlap without interference. This overlap of the scanned portions ensures that the entire surface is analyzed. The position of scanners relative to the inspection surface may be changed in between the scans and, in some embodiments, even during the scan. This approach allows precise scanning of large surfaces.

20 Claims, 12 Drawing Sheets

COMBINED SURFACE INSPECTION USING MULTIPLE SCANNERS

BACKGROUND

Inspecting surfaces of large components is essential for many applications, such as forming composite materials or, more specifically, fiber-reinforced materials. Typically, precision of an inspection tool is inversely proportional to its field of measurement. In other words, an inspection tool with a smaller field of measurement produces a more precise measurement than a tool with a larger field of measurement. At the same time, a smaller field of measurement results in a smaller inspected area during each scan.

While multiple inspection tools can be used in parallel for inspection of large surfaces, simultaneous operation of these tools can be challenging. For example, two adjacent inspection tools operating at the same time can interfere with each other. This interference can be particularly severe with optical inspection tools that may have overlapping fields of measurements to ensure inspection of the entire surface. As such, methods and systems for inspecting large surfaces using multiple scanners in a precise, accurate, and efficient manner are needed.

SUMMARY

Provided are methods and systems for inspecting surfaces of various components, such as evaluating height deviations on these surfaces. A method involves aggregating inspection data from multiple line scanners into a combined data set. This combined data set represents a portion of the surface that is larger than the field of measurement any one of the scanners. Furthermore, each pair of adjacent scanners operate at different periods of time to avoid interference. Because operating periods are offset, surface portions scanned by the pair of adjacent scanners can overlap without interference. This overlap of the scanned portions ensures that the entire surface is analyzed. The position of scanners relative to the inspection surface may be changed in between the scans and, in some embodiments, even during the scan. This approach allows precise scanning of large surfaces.

In some embodiments, a method of inspecting a surface of a component comprising aligning a first line scanner and a second line scanner relative to each other and to the surface of the component such that the field of measurement of the first line scanner partially overlaps with the field of measurement of the second line scanner. The method then proceed with scanning a first portion of the surface using the first line scanner during a first period such that scanning the first portion produces a first data set corresponding to the first portion. The method also procced with scanning a second portion of the surface using the second line scanner during a second period offset relative to the first period such that scanning the second portion produces a second data set corresponding to the second portion. The method then involves aggregating the first data set and the second data set into a combined data set.

In some embodiments, the first period does not overlap with the second period. The second period may start immediately after the first period. Alternatively, the first period may partially overlap with the second period. Some overlap between the periods may be allowed if this overlap does not cause substantial interference with scanning. For example, the overlap may be less than 20% or even less that 10% of each of the first period and the second period. Furthermore, the process of obtaining the data set may be based on integrating response over each entire period and some overlap may have only minimal impact.

In some embodiments, the field of measurement of the first line scanner is co-linear with the field of measurement of the second line scanner. More specifically, the first portion of the surface may be co-linear to the second portion of the surface. For example, the inspected surface may remain stationary with respect to the scanners while obtaining both data sets resulting in both portions being co-linear. Alternatively, the first portion of the surface may be parallel and offset with the second portion of the surface. For example, the inspected surface may move with respect to the scanners in the direction that is, for example, perpendicular to the field of measurements of the scanners.

In some embodiments, the combined data set comprises a first non-overlapping portion of the first data set and a second non-overlapping portion of the second data set. The combined data set may further comprise a combination of a first overlapping portion of the first data set and a second overlapping portion of the second data set. For example, the combination of the first overlapping portion of the first data set and the second overlapping portion of the second data set may be an average of the first overlapping portion of the first data set and the second overlapping portion of the second data set.

In some embodiments, aggregating the first data set and the second data set comprises spatially aligning the first data set and the second data set. This spatial alignment may be performed based on the position of the scanners relative to the surface of the inspected component or, more specifically, based on the positions of the field of measurements relative to that surface.

In some embodiments, the component changes position relative to the first line scanner while obtaining the second data set. More specifically, the component may change position relative to the first line scanner while obtaining the first data set. For example, the component may be moved relative to the first line scanner and relative to the second line scanner. The component may be moved in the direction perpendicular to the field of measurement of the first line scanner.

In some embodiments, the method further comprises scanning a third portion of the surface using the first line scanner during a third period such that scanning the third portion produces a third data set corresponding to the third portion. The third period is offset relative to the first period and being offset relative to the second period.

In some embodiments, the method may further comprise scanning a third portion of the surface using a third line scanner during the first period such that scanning the third portion produces a third data set corresponding to the third portion. The field of measurement of the third line scanner partially overlaps with the field of measurement of the second line scanner. In these embodiments, the third data set is aggregated together with the first data set and the second data set. The field of measurement of the third line scanner may be co-linear with the field of measurement of the first line scanner.

In some embodiments, the method further comprises forming the component. Obtaining the first data set, obtaining the second data set, and generating the combined data set may be performed in line with forming the component. The component may be a composite structure.

Provided also is a method of aggregating data sets obtained from multiple line scanners used for inspecting a surface of a component. The method comprises aligning the multiple line scanners in an array for a linear inspection of the surface such that field of measurements of each pair of adjacent line scanners of the multiple line scanners overlap. The array may be a linear array. The field of measurements of these scanners may be collinear and extend along the linear array.

The method proceeds with scanning the surface using the multiple line scanners such that scanners in each pair of the adjacent line scanners operate at different time periods. The method then proceed with aggregating the data sets produced by the multiple line scanners during scanning the surface into a combined data set.

In some embodiments, the method further comprises changing the position of the multiple line scanners relative to the surface and repeating scanning the surface using the multiple line scanners. Scanning the surface using the multiple line scanners may be repeated after a period determined based on a speed of changing position of the multiple line scanners relative to the surface.

Also provided is an inspection system for inspecting a surface of a component. In some embodiments, the system comprises a first line scanner, a second line scanner, and a system controller. The first line scanner is used for scanning a first portion of the surface during a first period and producing a first data set. The second line scanner is used for scanning a second portion of the surface during a second period and producing a second data set. The field of measurement of the first line scanner partially overlaps with the field of measurement of the second line scanner. Furthermore, the first period is offset relative to the second period. The system controller is used for aggregating the first data set and the second data set into a combined data set.

In some embodiments, the inspection system further comprises a motion device for moving the first line scanner and the second line scanner relative to the component. The inspection system may further comprise an encoder for determining position of at least one of the first line scanner and the second line scanner relative to the component. The system controller of the inspection system may comprise a data set aggregator, a memory, and an analyzing module. The data set aggregator may be operable to aggregate the first data set and the second data set into the combined data set. The memory may be operable to store the combined data set. Finally, the analyzing module may be operable to analyze the combined data set.

These and other embodiments are described further below with reference to the figures.

DETAILED DESCRIPTION

Figure 1A:
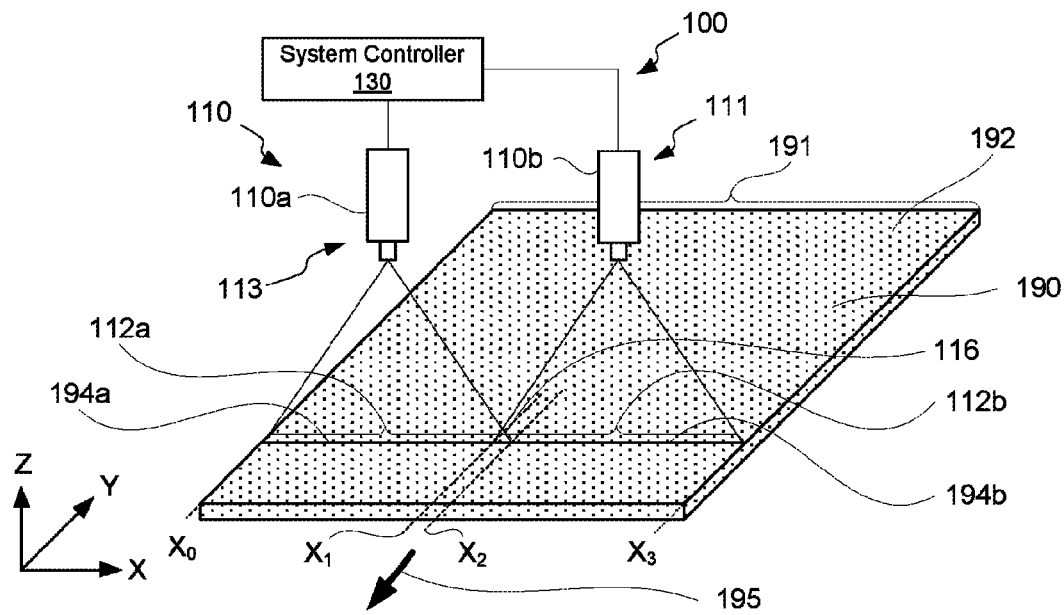
FIG. 1A is a schematic perspective view an inspection system comprising an array of two scanners scanning the surface of an inspected component, in accordance with some embodiments.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Introduction

Various inspection tools may be used for scanning surfaces. The scanning may be used to determine height deviations and other surface characteristics. One example of such inspection tools is a line scanner, which may be also referred to as a profilometer. During each scan, a line scanner produces a data set corresponding to the scanned portion of the surface. The line scanner may be moved relative to the scanned surface by moving the scanners, surface, or both. The movement may occur after completing each scan and/or during the actual scan. For example, a line scanner may be supported by a robot arm above a surface and scans may be triggered as the robot arm moves along the surface. The movement may proceed during each scan and in between scans (e.g., when another scanner is operational). Alternatively, a line scanner may be in a fixed position measuring a moving surface, such as a conveyor belt or a moving web (e.g., in a roll-to-roll process). As the scanner moves along the surface and produces new data sets, these sets may be aggregated into a collective surface representation. Each scan may be triggered at a fixed time-based frequency or using some external trigger sources, such as an encoder or a system controller.

Line scanners have finite sizes of their field of measurements. These field of measurements often smaller than dimensions of the scanned surface, especially for large component common in aircraft, automotive, and other industries. Furthermore, line scanners with small field of measurements (e.g., 2 inches) may be used to ensure precise measurements. As such, multiple scanners may be arranged into an array to cover a desired scan dimension/width. Multiple data sets produced by this array of scanners are aggregated together to produce a combined data set.

During a scan, a line scanner projects a line of light on an inspected surface and captures an optical image of the illuminated portion of the surface. In some embodiments, multiple images may be captured during the same scan period at a high frame rate. The illuminated portion of the surface may be referred to as a scanned portion. The size of this portion depends on the size of the field of measurement of the scanner and, also, on the position of the line scanner relative to the surface. Triangulation may be used by the line scanner to compute various high-accuracy surface characteristics (e.g., height deviations) from these optical images. These characteristics may be computed at fixed spacing along the projected line of light. The line scanner may output a data set, which may be in form of a 1D array of data values. In some embodiments, the data set represents height values along the projected line of light.

When the dimension of an inspected surface exceeds the field of measurement size of an individual scanner, multiple scanners may be placed side-by-side to cover the entire dimension. The fields of measurement of adjacent scanners may overlap to ensure no gaps in inspection. However, overlaps in the illuminated/inspected surface portions may cause various interferences in captured optical images. Avoiding overlap in the inspected portions may not be an option in situations when the entire surface needs to be inspected. For example, it has been found that a gap of at least 50 millimeters may be needed between two adjacent inspected portions to substantially avoid the interference. In other words, a portion of the surface, which is at least 50 millimeters wide, will not be inspected. This may not be acceptable for many types of surface inspections.

It has been found that the interference between two adjacent scanners can be reduced or even eliminated when these scanners are operated at different periods or, more specifically, at two periods that are offset with respect to each other. This feature may be referred to as a time-based operational offset of adjacent scanners. With the time-based offset, the field of measurements of adjacent scanners may be positioned next to each other and even overlap without interference.

In some embodiments, the inspected surface is moving relative to the line scanners. For purposes of this disclosure, the movement of the inspected surface relative to the line scanners includes all possible options, unless specifically noted: (a) moving the inspected surface while the line scanners remain stationary; (b) moving the line scanners while the inspected surface remain stationary; and (c) moving both the inspected surface and the line scanners. In the latter example, the inspected surface and the line scanners may move along the same direction. The focus here is the relative movement of the inspected surface to the line scanners. In these embodiments, inspection gaps will be formed (in the direction of the movement) because the time-based offset operation of the scanners. Specifically, after scanning a first portion using a first line scanner, the first line scanner may be turned off for a short period while a second line scanner (adjacent to the first line scanner) is performing its scan. A portion of the surface moving past the field of measurement of the first line scanner during the period will be uninspected. This portion may be referred to a gap between two portions inspected by the same line scanner. However, because each scan period is very short, these gaps will be very small and generally much smaller than the physical offset needed to avoid interference (described above). Furthermore, the gap can be controlled by changing the movement speed and/or scan duration.

Overall, time-based offsets for interference prevention may be selected based on the movement speed and scan duration. For purposes of this disclosure, $v_{max}$ is defined as the maximum achievable movement speed (measured in millimeter per seconds), e—scan duration (measured in seconds), $\Delta t$—time delay between beginning of two consecutive scans for the same scanner (trigger spacing in time for the first line scanner or the second line scanner, measured in seconds), $\Delta d$—uninspected gap width for the same scanner (physical trigger spacing for the first line scanner or the second line scanner, and measured in millimeters).

Applying these parameters to an example of two scanners, the scan duration (e) may not exceed a half of the trigger spacing ($\Delta t$), $e \leq \frac{1}{2}\Delta t$. For this example, the scan of the first line scanner may end before starting the scan with the second line scanner. The scan durations for both scanners may be the same and so is the trigger spacing. In some embodiments, the end of the first scan may substantially coincide with the beginning of the second scan, $e \sim \frac{1}{2}\Delta t$. Alternatively, some delay may be provided after the end of the first scan and before the beginning of the second scan, $e < \frac{1}{2}\Delta t$. In some embodiments, the scans may overlap in time, $e > \frac{1}{2}\Delta t$.

Furthermore, the correlation between the time delay between scans (for the same scanner), uninspected gap width, and movement speed may be in accordance with the following: $\Delta t \geq \Delta d/vmax$. The uninspected gap ($\Delta d$) may be selected by down-sampling a signal from a linear encoder to trigger the line scanners at a fixed pitch. The time delay between scans ($\Delta t$) may be variable based on the variable machine speed and fixed pitch.

Overall, surface inspection can be substantially enhanced by using multiple time-based offset line. In part, the rate at which a surface can be scanned can be increased, proportionally to the number of line scanners in one array. With this approach, line scanners with fine resolution can be used while using a larger coverage area that would typically only be possible with larger range lower resolution laser scanners. Placing line scanners in an array can enhance the coverage and, therefore, increase the rate at which a surface can be scanned.

Inspection System Examples

FIG. 1A is a schematic perspective view of inspection system 100 comprising first line scanner 110a and second line scanner 110b, in accordance with some embodiments. Inspection system 100 is shown in process of scanning surface 192 of inspected component 190. It should be noted that inspected component 190 is not a part of inspection system 100. Inspected component 190 is presented in FIG. 1A and some other figures simply as a reference and to illustrate various features of inspection system 100, such as field of measurement 112a of first line scanner 110a and field of measurement 112b of second line scanner 110b.

Figure 1B:
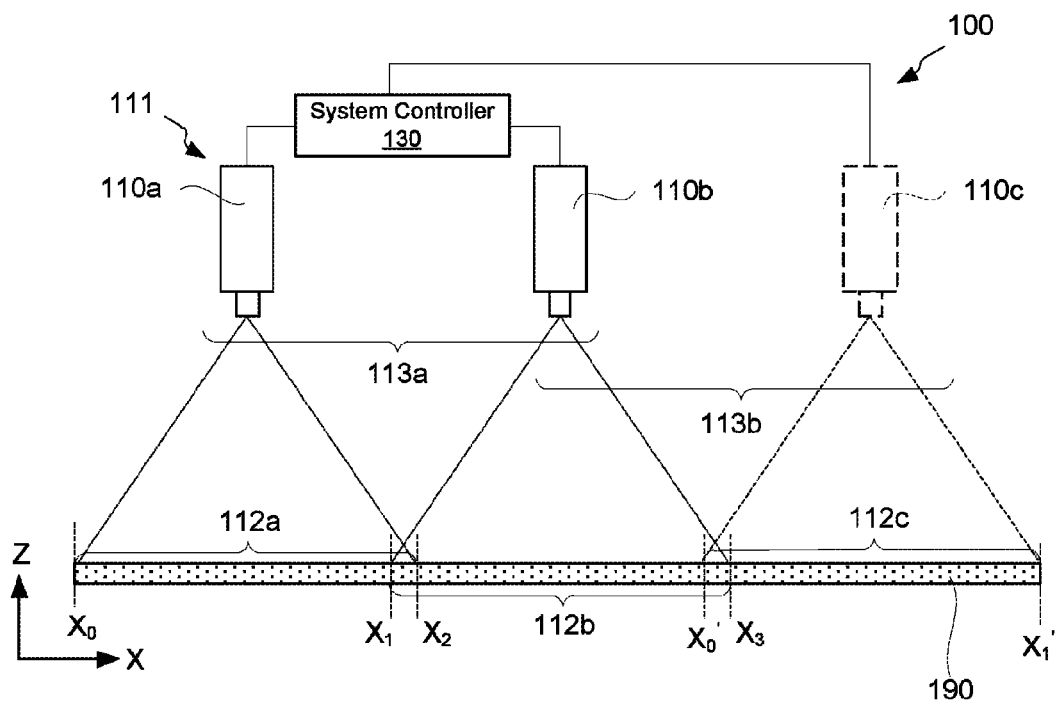
FIG. 1B is a schematic side view an inspection system comprising an array of three scanners scanning the surface of an inspected component, in accordance with some embodiments.

Inspection system 100 shown in FIG. 1A comprises first line scanner 110a and second line scanner 110b. In some embodiments, inspection system 100 may include one or more additional scanners, e.g., third line scanner 110C as shown in FIG. 1B. All scanners may be arranged into array 111, which extends in the X direction in FIGS. 1A and 1B.

First line scanner 110a and second line scanner 110b are arranged into array 111 or, more specifically, linear array 111 extending in the X direction. In this example, field of measurement 112a of first line scanner 110a is parallel to field of measurement 112b of second line scanner 110b or, more specifically, field of measurement 112a of first line scanner 110a is collinear to field of measurement 112b of second line scanner 110b.

In some embodiments, each of first line scanner 110a and second line scanner 110b is operable to detect height deviations on surface 192 of inspected component 190 within its respective field of measurement 112a/112b. As shown in FIGS. 1A and 1B, first line scanner 110a has first field of measurement 112a defining first scanned portion 194a on surface 192. Second line scanner 110b is shown to have second field of measurement 112b defining second scanned portion 194b on surface 192. Each of first field of measurement 112a and second field of measurement 112b may be a line, in which case first line scanner 110a and second line scanner 110b may be also referred to as linear scanners.

Figure 1C:
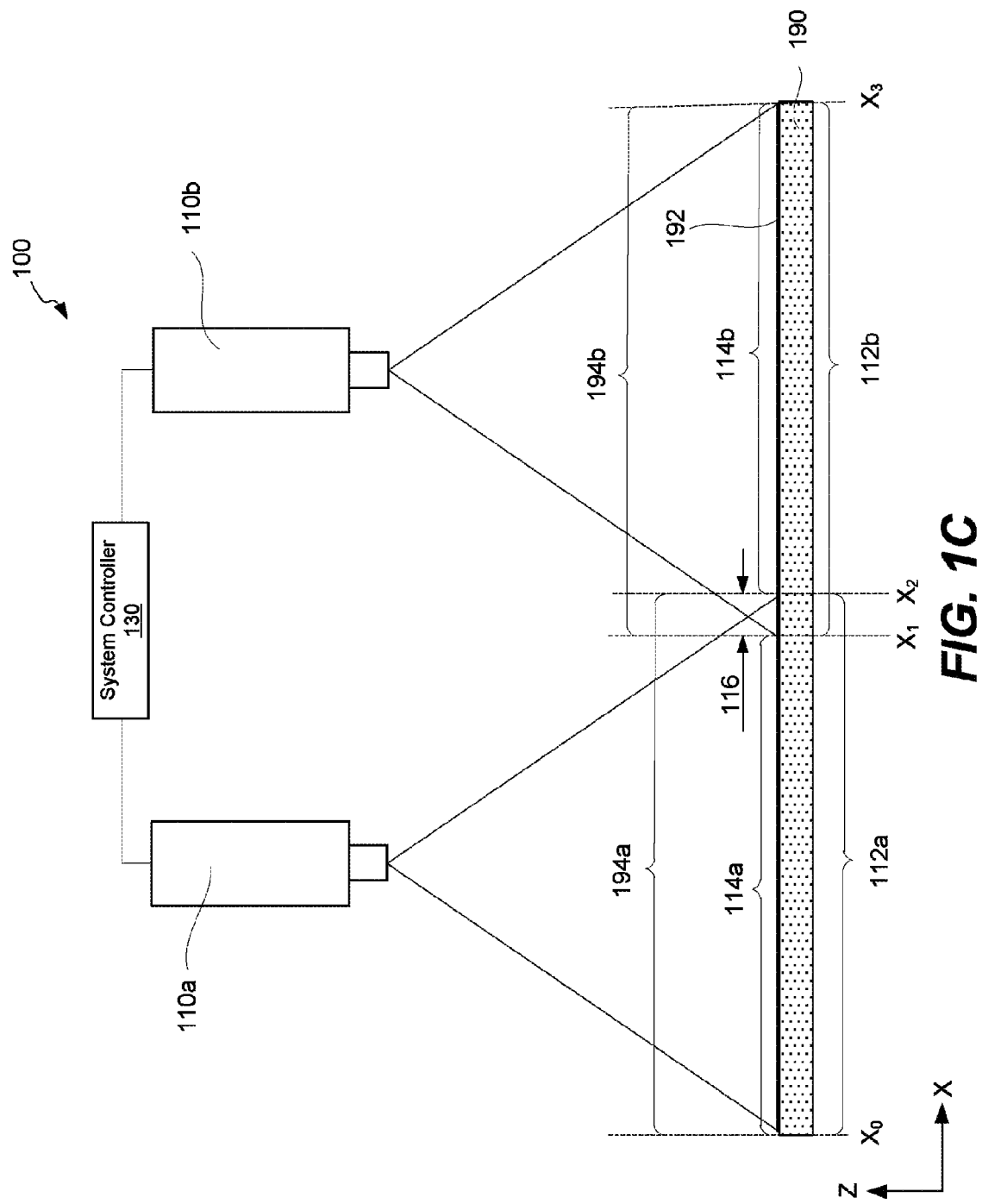
FIG. 1C is a schematic side view the inspection system of FIG. 1A, in accordance with some embodiments.

As shown in FIGS. 1A-1C, field of measurement 112a of first line scanner 110a partially overlaps with field of measurement 112b of second line scanner 110b. This overlap feature may be used to ensure that there are no gaps between inspected portions 194a and 194b at least in one direction, which the X direction in this example. It should be noted that even though field of measurements 112a and 112b overlap, there is no or very little interference between operation of first line scanner 110a and second line scanner 110b because their operating periods are offset and illuminated/inspected portions 194a and 194b do not overlap during the actual scans.

Referring to FIG. 1C, field of measurements 112a of first line scanner 110a extends in the X direction between points $X_0$ and $X_2$, while field of measurements 112B of second line scanner 110b extends in the X direction between points $X_1$ and $X_3$. Overlapping part 116 of these two field of measurements 112a and 112b extends between points $X_1$ and $X_2$. The size of overlapping part 116 may be between about 1% and 25% of the corresponding size of each of field of measurements 112a and 112b or, more specifically, between about 5% and 20%. The larger size of overlapping part 116 ensures that more of surface 192 is inspected and less precise alignment of the scanners is needed. On the other hand, increasing the size of overlapping part 116 may slow the overall inspection time and/or require additional scanners. It should be noted that field of measurements 112a and 112b are defined by characteristics of respective scanners 110a and 110b as well as position of these scanners 110a and 110b relative to each other and to inspected surface 192 (e.g., the distance between scanners 110a and 110b and inspected surface 192). In some other embodiments not shown in FIGS. 1A-1C, field of measurements 112a and 112b do not overlap. Instead, field of measurements 112a and 112b may simply touch at a point or even be separated by a gap that is less than 10% or even less than 5% of the corresponding size of each of field of measurements 112a and 112b.

Figure 1D:
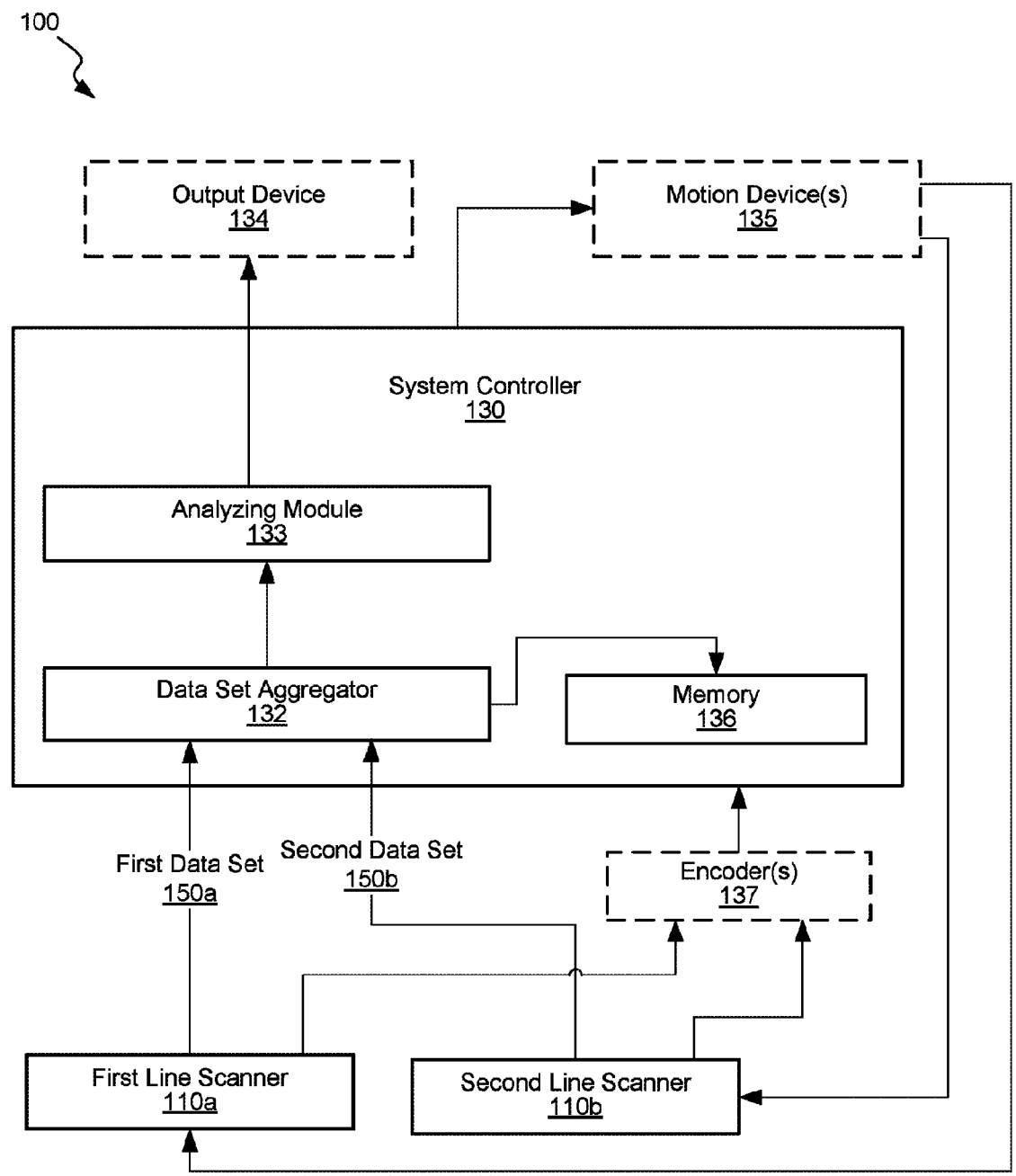
FIG. 1D is a schematic block diagram of the inspection system of FIG. 1A, in accordance with some embodiments.

FIG. 1D is a schematic block diagram of inspection system 100 of FIG. 1A, in accordance with some embodiments. First line scanner 110a and second line scanner 110b may be movable relative to inspected component 190. This movement may be manual. Alternatively, inspection system 100 may optionally include motion device 135 used for moving first line scanner 110a and/or second line scanner 110b relative to inspected component 190. Some examples of motion device 135 is a step motor, a linear table (e.g., Y-table), an X-Y table, a rotational device, or some other suitable devices. First line scanner 110a and second line scanner 110b may be moved together or independently from each other. For example, when first line scanner 110a scans inspected component 190, it may remain stationary relative to inspected component 190 while second line scanner 110b moves into a new position. Alternatively, first line scanner 110a and second line scanner 110b may remain stationary and inspected component 190 may be moved relative to first line scanner 110a and second line scanner 110b. In some embodiments, system controller 130 may send instructions to motion device 135 to change position of one or both scanners 110a and 110b relative to inspected component 190.

In some embodiments, inspection system 100 optionally includes one or more encoders 137 for determining positions of first line scanner 110a and/or second line scanner 110b (e.g., relative to inspected component 190). Furthermore, encoders 137 may be used for determining positions of first line scanner 110a and second line scanner 110b relative to each other, e.g., to facilitate establishing or changing a desired overlap, especially when first line scanner 110a and second line scanner 110b are movable with respect to each other. Alternatively, first the position of scanner 110a and second line scanner 110b may be fixed with respect to each other. These positions may be associated with each data set produced by first line scanner 110a and/or second line scanner 110b. Encoder 137 may continuously send information about positions of first line scanner 110a and/or second line scanner 110b to system controller 130, which may use this position information to initiate scans, associate positions with various data sets, and/or aggregate data sets.

System controller 130 of inspection system 100 may be used to control operation of first line scanner 110a and second line scanner 110b. System controller 130 may be also used to aggregate data sets received from first line scanner 110a and second line scanner 110b using, for example, data set aggregator 132. Data set aggregator 132 produces a combined data set for a data set received from first line scanner 110a and another data set received from second line scanner 110b. Combined data sets produced by data set aggregator 132 and, in some embodiments, other data may be stored in memory 136 of system controller 130. For example, memory 136 may also store data sets received from scanners 110a and 110b, information received from encoder 137 (e.g., scanner positions at the time of scanning). Memory 136 may also store various data points used for analyzing combined data sets, such as height tolerances.

Another optional component of system controller 130 is analyzing module 133. Analyzing module 133 may be used and configured to analyze combined data sets to determine, for example, height deviations that exceed tolerance. In some embodiments, analyzing module 133 may identify outliers and even construct outlier representation. In some embodiments, system controller 130 may send the outlier representation to output device 134, such as a display, printer, or another computer system.

Inspection Method Examples

Figure 2:
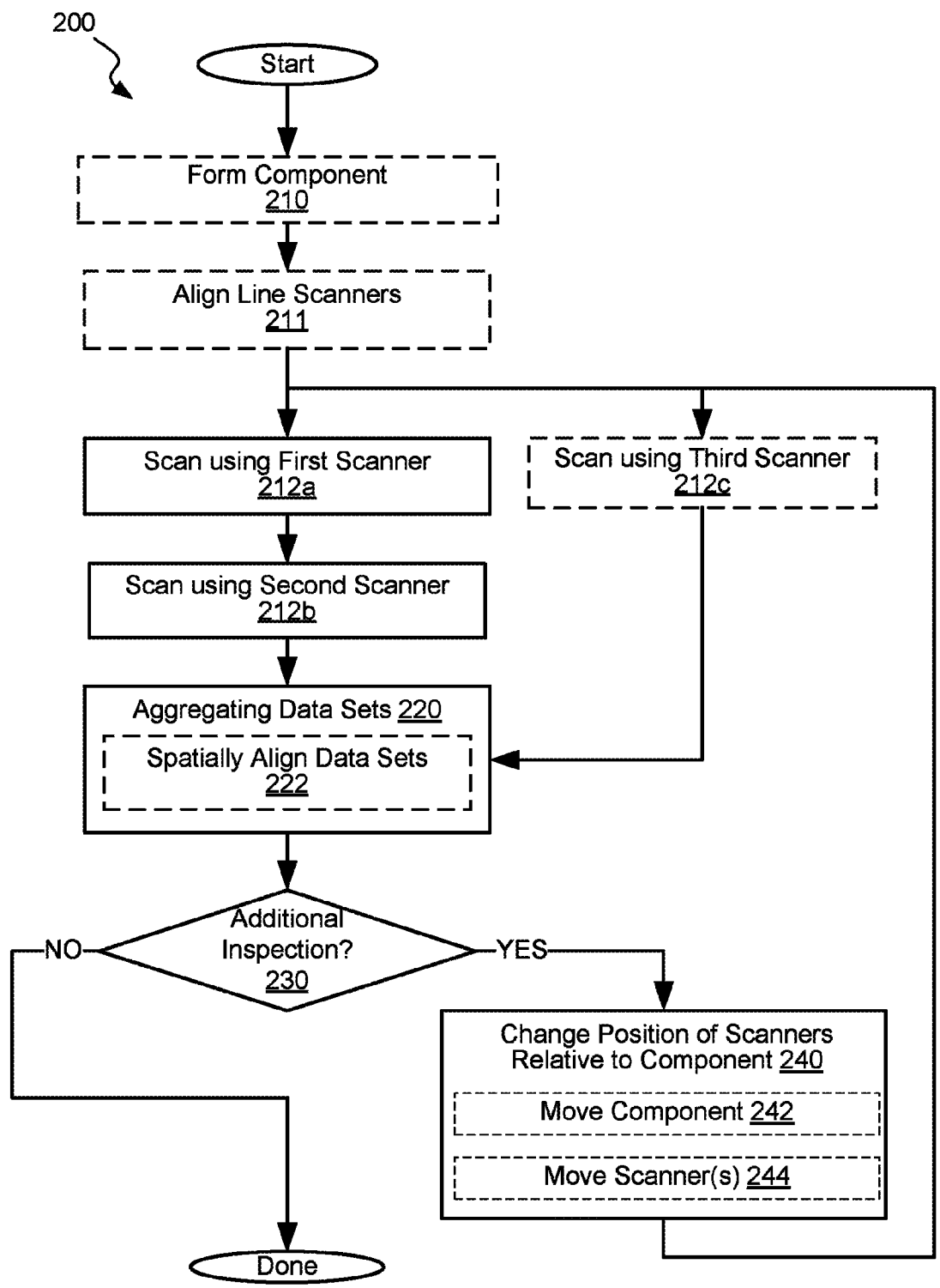
FIG. 2 is a process flowchart corresponding to a method of inspecting a surface of a component, in accordance with some embodiments.

FIG. 2 is a process flowchart corresponding to method 200 of inspecting surface 192 of component 190, in accordance with some embodiments. Some operations of method 200 may be performed using inspection 100 described above.

In some embodiments, method 200 may commence with forming component 190 during optional operation 210. For example, component 190 may be a composite structure formed from multiple plies. These plies may be flat sheets that are arranged into a layup. To shape the layup, the initially flat layup may be subjected to pressing into a die or bending the around a mold. Wrinkles and other height variations may occur in component 190 during its forming.

In some embodiments, scanning surface 192 is performed in line with forming component 190 during operation 210.

For example, operations 212a-212b as well as operation 220 may be performed and repeated while forming component 190, which may be referred to as in-process inspection. For example, surface 192 may be scanned after adding each ply and, more specifically, while adding each ply to detect any in process defects. Surface 192 may be further scanned while shaping the layup.

In some embodiments, method 200 involve aligning first line scanner 110a and second line scanner 110b relative to each other and relative to surface 192 of component 190 during optional operation 211. For example, first line scanner 110a and second line scanner 110b may be attached to a support disposed over surface 192 of component 190. After completing operation 211, field of measurement 112a of first line scanner 110a may partially overlap with field of measurement 112b of second line scanner 110b as, for example, shown in FIGS. 1A-1C and discussed above.

Returning to FIG. 2, method 200 may involve scanning first portion 194a of surface 192 using first line scanner 110a during operation 212a. This operation 212a is performed during first period 160a and produces first data set 150a corresponding to representing first portion 194a. For example, during operation 212a, first line scanner 110a may illuminate first portion 194a and capture one or more optical images of first portion 194a to determine various characteristics of this portion, such as height deviations. First portion 194a corresponds to field of measurement 112a of first line scanner 110a during first period 160a.

Method 200 may involve scanning second portion 194b of surface 192 using second line scanner 110b during operation 212b. This operation 212b may be similar to operation 212a described above but it is performed during second period 160b offset relative to first period 160a. Also, operation 212b produces second data set 150b corresponding to second portion 194b. Second portion 194b corresponds to field of measurement 112b of second line scanner 110b during second period 160b. The offset between first period 160a and second period 160b is used to reduce interference between these two scans.

Figure 3A:
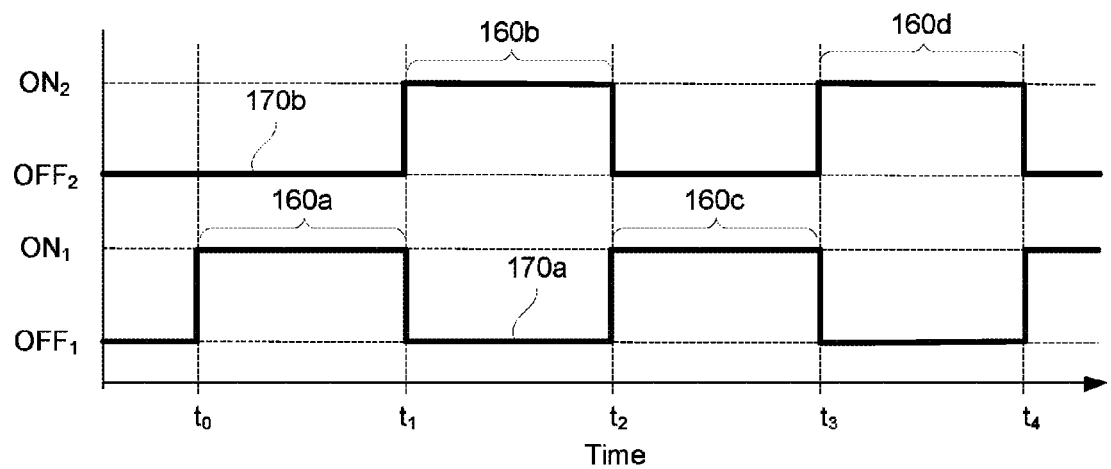
FIGS. 3A-3C are different examples of an operating sequence diagram of two scanners, in accordance with some embodiments.
Figure 3B:
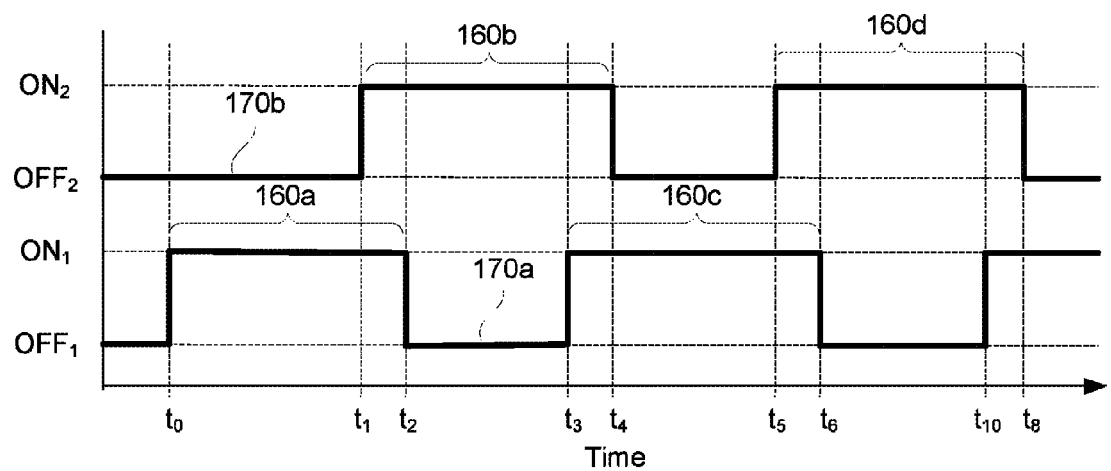
Figure 3C:
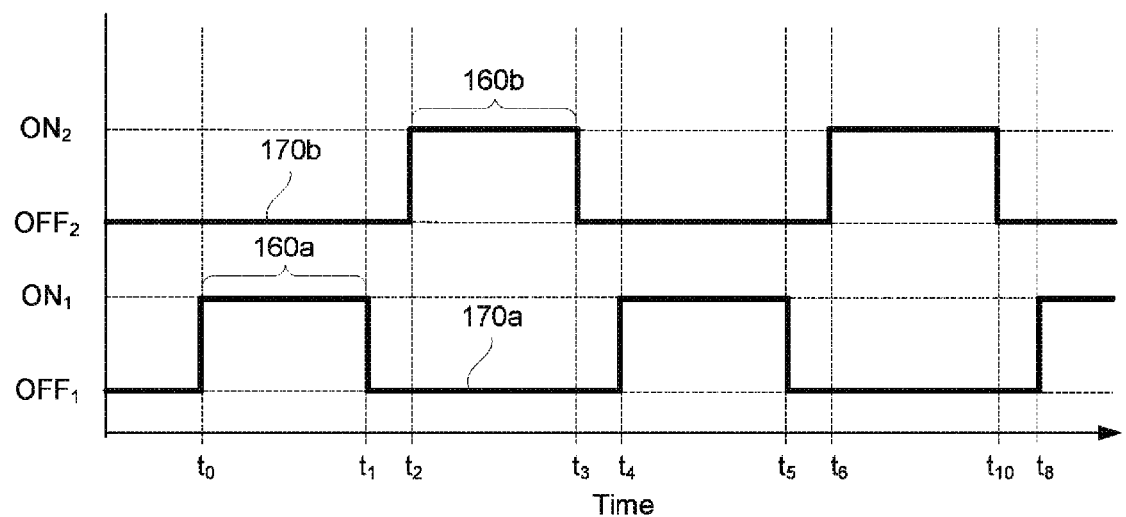

FIGS. 3A-3C illustrate three examples of operating sequences 170a and 170b in which first period 160a being offset relative to second period 160b. Specifically, first operating sequence 170a corresponds to first line scanner 110a, while second operating sequence 170b corresponds to second line scanner 110b.

Referring to FIG. 3A, first period 160a starts at $t_0$ and ends at $t_1$, while second period 160b starts at $t_1$ and ends at $t_2$. As such, the end of first period 160a coincides with the beginning of second period 160b in this example. In other words, second period 160b starts immediately after first period 160a. Furthermore, first period 160a does not overlap with second period 160b in this example.

Scanning using first line scanner 110a may be repeated during third period 160c, which starts at $t_2$ and ends at $t_3$, as shown in FIG. 3A. The end of second period 160b coincides with the beginning of third period 160c in this example. In other words, the trigger delay (the duration between the begging of two scans) of first line scanner 110a is equal to a sum of first period 160a and second period 160b. In a similar manner, scanning using second line scanner 110b may be repeated during fourth period 160d, which starts at $t_3$ and ends at $t_4$. One having ordinary skill in the art would understand that these scans using first line scanner 110a and second line scanner 110b may continue to repeat with the established offset.

In some embodiments, first period 160a is equal to second period 160b. In these embodiments, the trigger delay is double the scan period. Alternatively, first period 160a may be different from second period 160b.

FIG. 3B illustrates another example of first period 160a being offset relative to second period 160b. In this example, first period 160a overlaps with second period 160b. Specifically, first period 160a starts at $t_0$ and ends at $t_2$, while second period 160b starts at $t_1$ and ends at $t_4$. As such, second period 160b starts (at $t_1$) before first period 160a ends (at $t_2$). The overlap (between $t_1$ and $t_2$) may be substantially smaller than each first period 160a and second period 160b to reduce interference between two scans. For example, the overlap may be less than 10% or even less than 5% of each first period 160a and second period 160b.

Furthermore, when scanning using first line scanner 110a is repeated during third period 160c, which starts at $t_3$ and ends at $t_6$, second period 160b also overlaps with third period 160c. In a similar manner, third period 160c also overlaps with fourth period 160d in addition to overlapping with second period 160b.

FIG. 3C illustrates yet another example of first period 160a being offset relative to second period 160b. In this example, first period 160a does not overlap with second period 160b and second period does not start immediately after first period 160a. There is a delay between first period 160a and second period 160b. Specifically, first period 160a starts at $t_0$ and ends at $t_1$, while second period 160b starts at $t_2$ and ends at $t_2$. As such, there is delay ($t_1$ to $t_2$) between the end of first period 160a and the start of second period 160b. The delay may be substantially smaller than each first period 160a and second period 160b to reduce interference between two scans. For example, the delay may be less than 10% or even less than 5% of each first period 160a and second period 160b.

As noted above, while scanning surface 192 using multiple line scanners 110, their field of measurements 112 may overlap. Referring to FIGS. 1A-1C, field of measurement 112a of first line scanner 110a may partially overlap with field of measurement 112b of second line scanner 110b. Specifically, field of measurement 112a of first line scanner 110a extends between $X_0$ and $X_2$, while field of measurement 112b of second line scanner 110b extending between $X_1$ and $X_3$. Overlapping part 116 extends between $X_1$ and $X_2$. Overlapping part 116 ensures that there are no gaps in scanning surface 192 at least in the X direction.

Furthermore, referring to FIG. 1A, field of measurement 112a of first line scanner 110a may be co-linear with field of measurement 112b of second line scanner 110b. This co-linearity feature may be helpful while aggregating first data set 150a and second data set 150b into combined data set 151 and to avoid the need for offsetting and other manipulations with first data set 150a and second data set 150b. Collinearity of field of measurements 112a and 112b may translate into collinearity of inspected portions 194a and 194b if, for example, inspected component 190 is not moved relative to scanners 110a and 110b during or between scanning inspected portions 194a and 194b. However, if inspected component 190 is moved relative to scanners 110a and 110b during or between scanning inspected portions 194a and 194b, then first portion 194a may be parallel and offset with respect to second portion 194b of surface 192.

Returning to FIG. 2, method 200 involves aggregating first data set 150a and second data set 150b into combined data set 151 during operation 220. First data set 150a corresponds to first portion 194a and defined by field of measurement 112a of first line scanner 110a during the actual scan (e.g., first period 160a) as schematically shown in FIG. 1A. Similarly, second data set 150b corresponds to second portion 194b and is defined by field of measurement 112b of second line scanner 110b during the actual scan (e.g., second period 160b), also schematically shown in FIG. 1A. Combined data set 151 corresponds to both first portion 194a and second portion 194b. Referring to FIG. 1A, combined data set 151 represents a portion of surface 192 extending between $X_0$ and $X_3$. In some embodiments, combined data set 151 represent all portions extending along one dimension 191 of inspected component 190.

Aggregating first data set 150a and second data set 150b depend on relative positions of first portion 194a and second portion 194b, e.g., whether first portion 194a and second portion 194b overlap and/or offset with respect to each other. For example, FIGS. 1A-1C illustrate first portion 194a and second portion 194b, referring to overlapping part 116 illustrated in FIG. 1C and extending between $X_1$ and $X_2$.

Figures 4A, 4B, 4C:
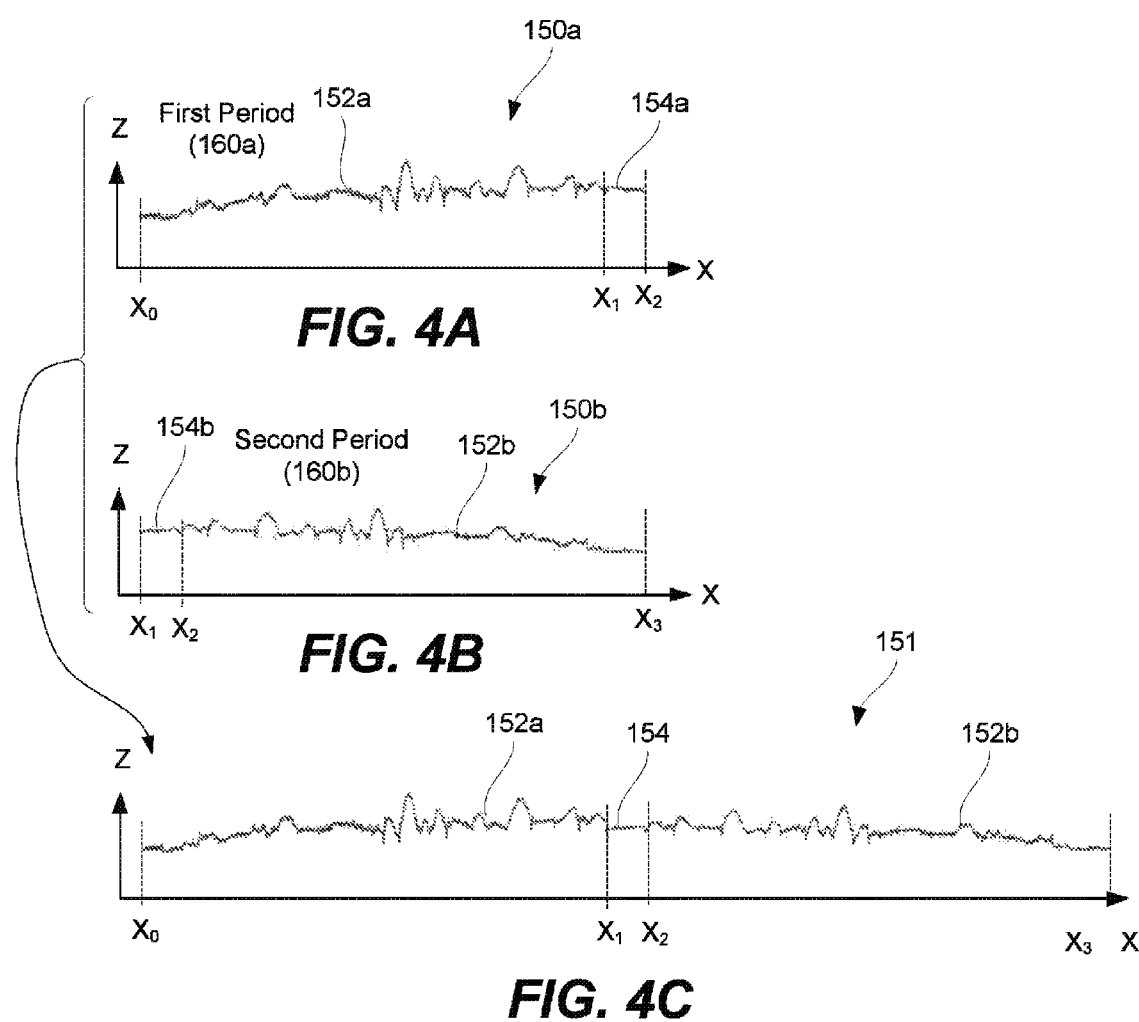
FIGS. 4A and 4B are schematic representation of two data sets obtained by the two scanners of the inspection system shown in FIG. 1A, in accordance with some embodiments.
FIG. 4C is a schematic representation of a combined data set produced by aggregating two data sets shown in FIGS. 4A and 4B, in accordance with some embodiments.

FIGS. 4A and 4B are schematic representation of first data set 150a and second data set 150b, in accordance with some embodiments. First data set 150a comprises first non-overlapping portion 152a and first overlapping portion 154a. First non-overlapping portion 152a corresponds to first non-overlapping part 114a (extending between $X_0$ and $X_1$ as shown in FIG. 1C) of first inspected portion 194a. First overlapping portion 154a corresponds to overlapping part 116 (extending between $X_1$ and $X_2$ as shown in FIG. 1C) of first inspected portion 194a.

Similarly, second data set 150b comprises second non-overlapping portion 152b and second overlapping portion 154b. Second non-overlapping portion 152b corresponds to second non-overlapping part 114b (extending between $X_2$ and $X_3$ as shown in FIG. 1C) of second inspected portion 194b. Second overlapping portion 154b corresponds to overlapping part 116 (extending between $X_1$ and $X_2$ as shown in FIG. 1C). It should be noted that first overlapping portion 154a of first data set 150a and second overlapping portion 154b of second data set 150b correspond to the same overlapping part 116 of inspected component 190. In other words, first overlapping portion 154a and second overlapping portion 154b may be viewed as a redundant data. When aggregating first data set 150a and second data set 150b, one of first overlapping portion 154a and second overlapping portion 154b may be ignored or an average of first overlapping portion 154a and second overlapping portion 154b may be used to represent overlapping part 116 of inspected surface 192.

FIG. 4C is a schematic representation of combined data set 151, in accordance with some embodiments. Combined data set 151 is a result of aggregating first data set 150a and second data set 150b during operation 220. Combined data set 151 includes first non-overlapping portion 152a of first data set 150a and second non-overlapping portion 152b of second data set 150b. Combined data set 151 also includes combined overlapping portion 154, which is derived from one or both of first overlapping portion 154a of first data set 150a and second overlapping portion 154b of second data set 150b. For example, combined overlapping portion 154 may be generated by selecting one of first overlapping portion 154a or second overlapping portion 154b. In another example, combined overlapping portion 154 may averaging first overlapping portion 154a and second overlapping portion 154b or, more specifically, data values in these overlapping portions.

In some embodiments, aggregating first data set 150a and second data set 150b comprises spatially aligning these data sets during optional operation 222 as shown in the flowchart of FIG. 2. This spatial alignment may be performed based on relative positions of first portion 194a and second portion 194b. For example, operation 222 may involve identifying overlapping part 116 in first portion 194a and second portion 194b and then identifying first non-overlapping portion 152a, first overlapping portion 154a, second non-overlapping portion 152b, and second overlapping portion 154b. It should be noted that the relative positions of first portion 194a and second portion 194b are determined, at least in part, by the alignment of first line scanner 110a and second line scanner 110b relative to each other and relative to surface 192 of component 190. As such, this alignment of first line scanner 110a and second line scanner 110b may be used for spatially aligning first data set 150a and second data set 150b. The above example refers to the spatial alignment of the data along the X axis. One having ordinary skills in the art would understand that alignment may be performed along other axes as well, such as along the Y axis, for example, to compensate for movement of inspected component 190 relative to first line scanner 110a and second line scanner 110b.

Returning to FIG. 2, method 200 may involve changing the position of scanners 110a and 110b relative to component 190 during operation 240. Specifically, operation 240, which may be referred to as changing scanner-to-component position operation 240, may involve moving component 190 while scanners 110a and 110b remain stationary as reflected by optional operation 242, which may be referred to as component moving operation 242. Alternatively, changing scanner-to-component position operation 240 may involve moving one or both scanners 110a and 110b while component 190 remains stationary as reflected by optional operation 244, which may be referred to as scanner moving operation 244. Furthermore, changing scanner-to-component position operation 240 may involve moving one or both scanners 110a and 110b and component 190 at the same time. In other words, changing scanner-to-component position operation 240 may include both component moving operation 242 and scanner moving operation 244, which may be performed at the same time. The moving during operation 242 and/or operation 244 may be in direction 195 perpendicular to field of measurement 112a of first line scanner 110a as, for example, schematically shown in FIG. 1A.

In some embodiments, component 190 may change its position relative to first line scanner 110a. It may happen while component 190 also changes its position relative to second line scanner 110b. For example, component 190 may change its position relative to first line scanner 110a and relative to second line scanner 110b at the same time. Alternatively, component 190 may change its position relative to first line scanner 110a while the relative position between component 190 and second line scanner 110b is maintained constant. For example, first line scanner 110a may be moved (independently from second line scanner 110b) relative to component 190, while second line scanner 110b maintains its relative position to component 190.

This movement (component 190 changing its position relative to first line scanner 110a) may be performed while scanning second portion 194b using second line scanner 110b during operation 212b. Furthermore, first portion 194a may be scanned using first line scanner 110a during this movement. In other words, component 190 may changing its position relative to first line scanner 110a while first line scanner 110a scans first portion 194a on surface 192 of component 190.

Figure 5A:
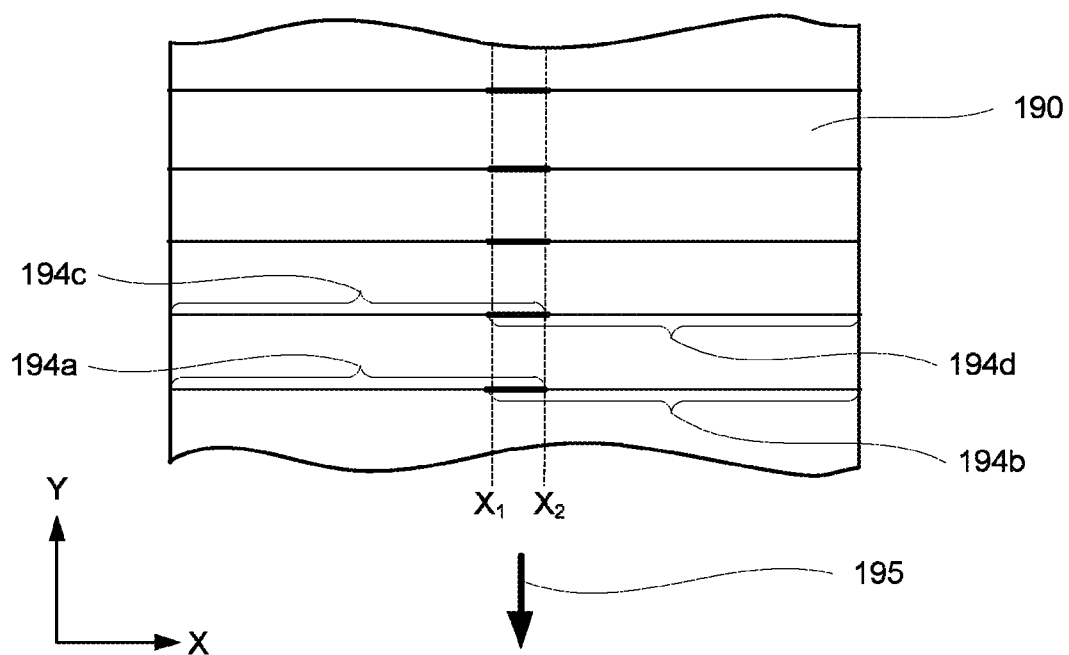
FIGS. 5A and 5B are schematic top views of an inspected component showing different positions of inspection portions on the surface of the inspected component, in accordance with some embodiments.
Figure 5B:
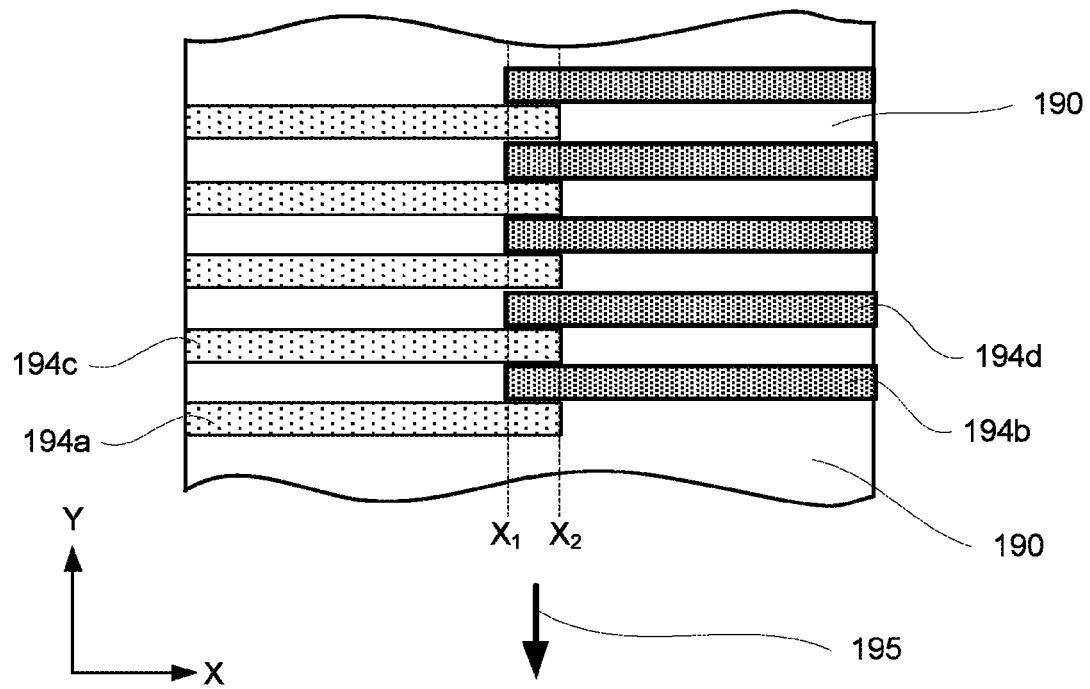

Returning to FIG. 2, after component 190 changes its position relative to first line scanner 110a, scanning surface 192 using first line scanner 110a may be repeated as reflected by decision block 230. The additional scanning may be performed during third period 160c offset relative to first period 160a and offset relative to second period 160b as described above with reference to FIGS. 3A-3C. The additional scanning produces third data set 150c corresponding to third portion 194c of surface 192. Different examples of third portion 194c and its position relative to first position 194a are shown in FIGS. 5A and 5B. Third portion 194c is offset relative to first portion 194a in the Y direction because component 190 changes its position relative to first line scanner 110a. In a similar manner, scanning surface 192 using second line scanner 110b may be repeated to scan fourth portion 194d. This scanning may be performed during fourth period 190d, which is offset relative to first period 160a, second period 160b, and third period 160c.

In the example illustrated in FIG. 5A, component 190 does not change its position relative to first line scanner 110a while first line scanner 110a performs scans. As such, first portion 194a and third portion 194c have linear profiles. In this example, component 190 may change its position relative to first line scanner 110a at other times, e.g., while second line scanner 110b scans second portion 194b. However, in this illustrated example, component 190 also does not changes its position relative to second line scanner 110b while second line scanner 110b performs scans. For example, first line scanner 110a and second line scanner 110b may move independently to each other during the overall operation.

FIG. 5B illustrates another example in which component 190 changes its position relative to first line scanner 110a while first line scanner 110a performs scans. As such, first portion 194a and third portion 194c have widths in the Y direction. Similarly, component 190 changes its position relative to second line scanner 110b while second line scanner 110b performs scans. As such, second portion 194b and fourth portion 194d have widths in the Y direction. Furthermore, the uninspected gap between each pair of adjacent portions inspected by the same scanner (e.g., between first portion 194a and third portion 194c and, separately, between second portion 194b and fourth portion 194d) in the Y direction may be smaller than the size of a typical surface imperfection in this direction. Furthermore, as stated above, the uninspected gap may be controlled and, in some embodiments, may be selected by down-sampling a signal from a linear encoder to trigger the line scanners at a fixed pitch.

The width of first portion 194a (in the Y direction) depends on the speed with which inspected component 190 moves relative to first line scanner 110a and duration of first period 160a. Likewise, the width of second portion 194b (in the Y direction) depends on the speed with which inspected component 190 moves relative to second line scanner 110b and duration of second period 160b. In some embodiments, the width of first portion 194a and/or second portion 194b may be between about 1 inch and 10 inches or, more specifically, between about 2 inches and 3 inches. The width of first portion 194a may be the same as the width of second portion 194b. In this example, the duration of first period 160a may be the same as the duration of second period 160b. Also, the speed with which inspected component 190 moves relative to the scanners may be the same during both periods.

In some embodiments, inspection system 100 comprises third line scanner 110c as schematically shown in FIG. 1B. Third line scanner 110c may form array 111 with first line scanner 110a and second line scanner 110b such that second line scanner 110b is disposed between first line scanner 110a and third line scanner 110c. As such field of measurement 112a of first line scanner 110a does not overlap with field of measurement 112c of third line scanner 110c and first line scanner 110a and third line scanner 110c may be operated at the same time. First line scanner 110a and second line scanner 110b form first pair of adjacent line scanners 113a. Second line scanner 110b and third line scanner 110c form second pair of adjacent line scanners 113b. As such, field of measurement 112b of second line scanner 110a may overlap with field of measurement 112c of third line scanner 110c. In this regard, operation of second line scanner 110b and third line scanner 110c should not have substantial overlaps. Furthermore, field of measurement 112a of first line scanner 110a may be collinear with field of measurement 112c of third line scanner 110c. In some embodiments, all three field of measurements 112a-112b may be collinear.

Figure 6A:
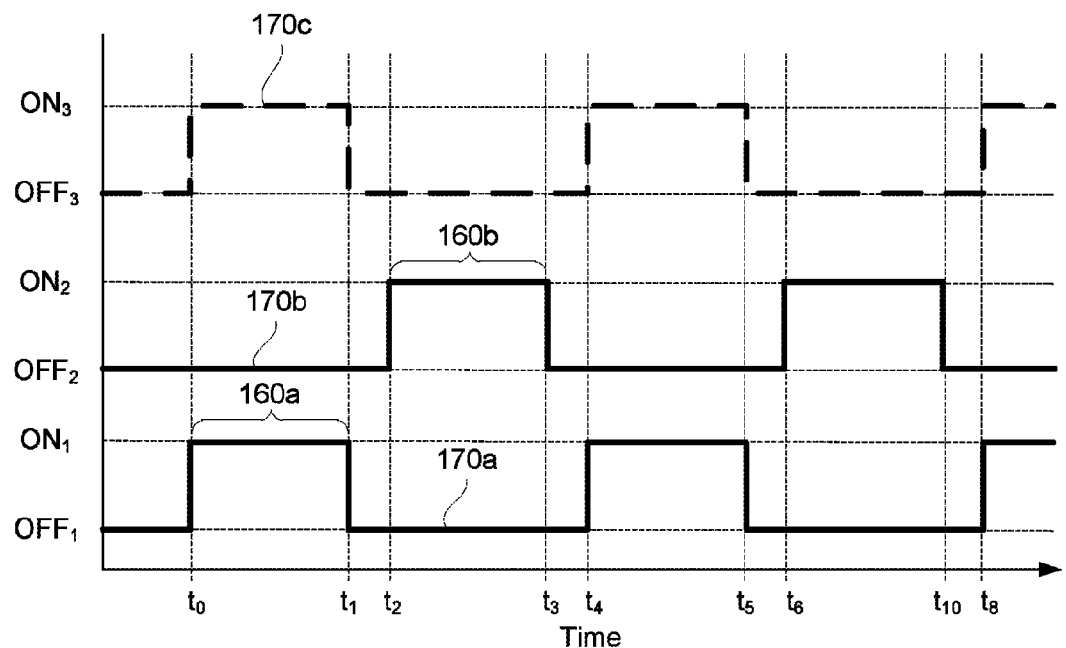
FIG. 6A is an example of an operating sequence diagram of three scanners, in accordance with some embodiments.

FIG. 6A illustrates one example operating sequences 170a-170c of three scanners 110a-110c. In this example, first line scanner 110a and third line scanner 110c operate simultaneously during first period 160a. In other words, operating sequence 170a of first line scanner 110a may be the same as operating sequence 170b of third line scanner 110c but different from operating sequence 170b of second line scanner 110b. First period 160a is offset relative to second period 160b, during which second line scanner 110b is operational.

Figure 6B:
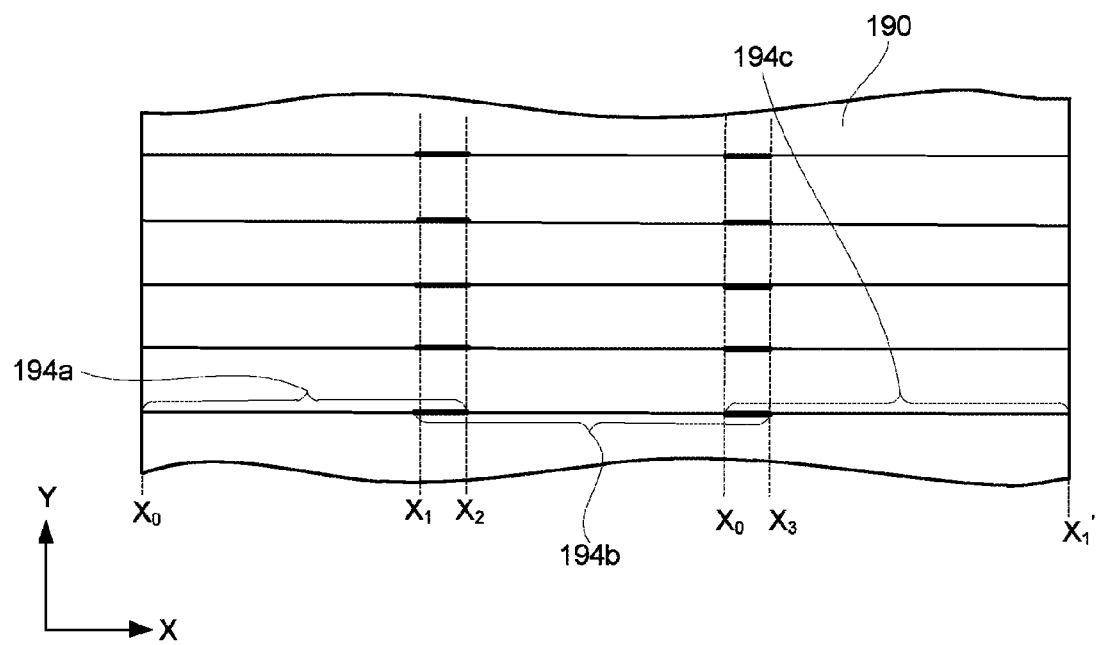
FIG. 6B is a schematic top view of an inspected component showing different positions of inspection portions on the surface of the inspected component, in accordance with some embodiments.

In these three-scanner embodiments, method 200 further comprises scanning third portion 194c of surface 192 using third line scanner 110c. The location of third portion 194c relative to first portion 194a and second portion 194b is illustrated in FIG. 6B. This scanning produces third data set 150c corresponding to third portion 194c. This example of third data set 150c is aggregated 220 together with first data set 150a and second data set 150b. This operating example should not be confused with another example where third data set 150c is obtained during an additional scan of first line scanner 110a, which is described above.

Examples of Controller Computer Inspection Systems

Figure 7:
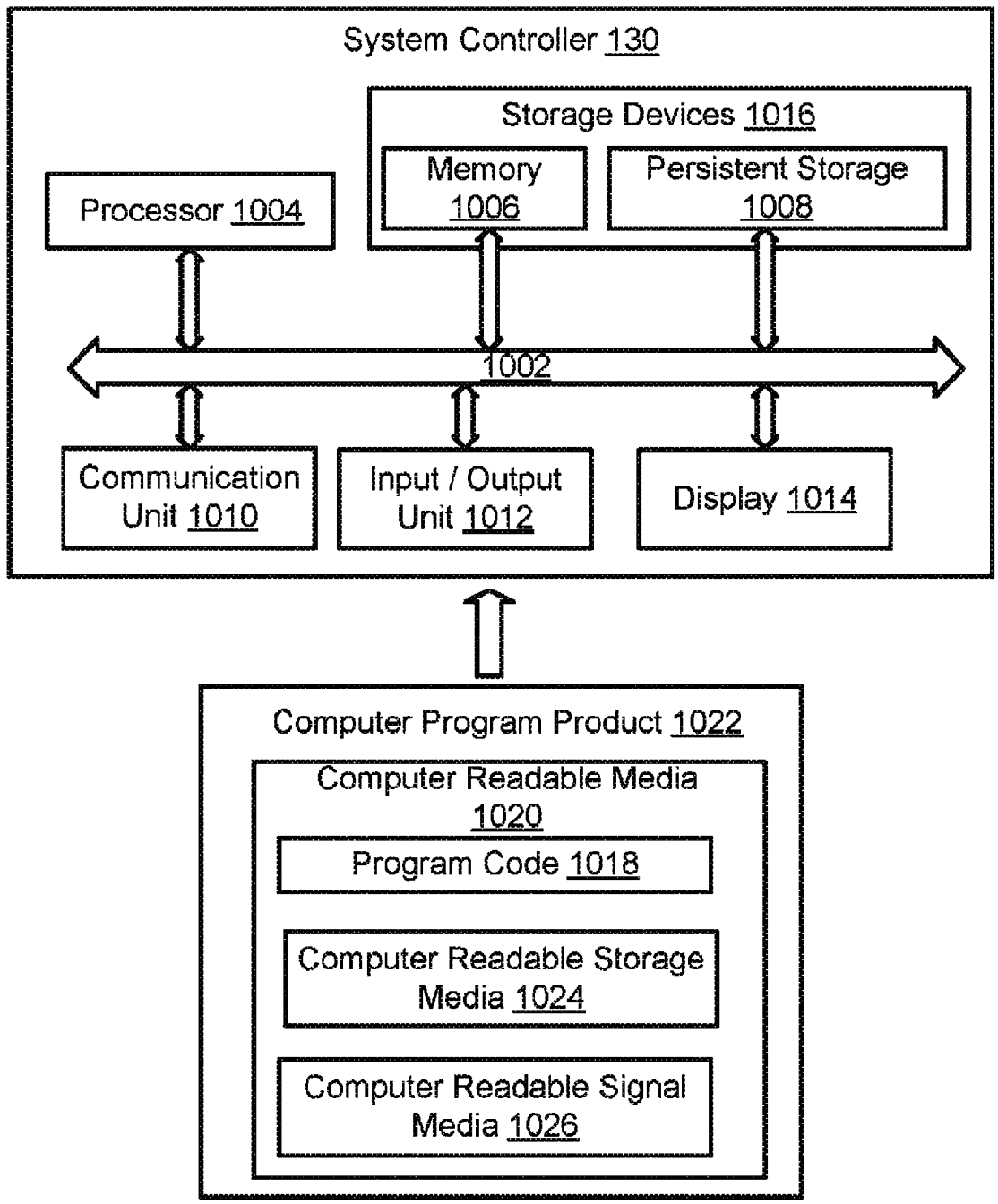
FIG. 7 is an illustration of a data processing inspection system, in accordance with some embodiments.

Turning now to FIG. 7, an illustration of system controller 130 of inspection system 100 is presented in accordance with some embodiments. System controller 130 may be used to implement one or more computers used in a system controller of or other components of various examples of inspection system 100 described above. In some embodiments, system controller 130 includes communications framework 1002, which provides communications between processor unit 1004, memory 1006, persistent storage 1008, communications unit 1010, input/output I/O unit 1012, and display 1014. In this example, communications framework 1002 may take the form of a bus inspection system.

Processor unit 1004 serves to execute instructions for software/instructions that may be loaded into memory 1006. These instructions may be use for carrying out various operations of method 200 described above with reference to FIG. 2, such as aligning first line scanner 110a and second line scanner 110b relative to each other and to surface 192 of component 190 such that field of measurement 112a of first line scanner 110a partially overlaps with field of measurement 112b of second line scanner 110b; scanning 212a first portion 194a of surface 192 using first line scanner 110a during first period 160a such that scanning 212a first portion 194a produces first data set 150a corresponding to first portion 194a; scanning 212b second portion 194b of surface 192 using second line scanner 110b during second period 160b offset relative to first period 160b such that scanning 212b second portion 194b produces second data set 150b corresponding to second portion 194b; and aggregating 220 first data set 150a and second data set 150b into a combined data set 151.

Processor unit 1004 may be a number of processors, a multi-processor core, or some other type of processor, depending on the particular implementation. Memory 1006 and persistent storage 1008 are examples of storage devices 1016. A storage device is any piece of hardware that is capable of storing information, such as, for example, without limitation, data, program code in functional form, and/or other suitable information either on a temporary basis and/or a permanent basis. Storage devices 1016 may also be referred to as computer readable storage devices in these illustrative examples. Memory 1006, in these examples, may be, for example, a random access memory or any other suitable volatile or non-volatile storage device. Persistent storage 1008 may take various forms, depending on the particular implementation. For example, persistent storage 1008 may contain one or more components or devices. For example, persistent storage 1008 may be a hard drive, a flash memory, a rewritable optical disk, a rewritable magnetic tape, or some combination of the above. The media used by persistent storage 1008 also may be removable. For example, a removable hard drive may be used for persistent storage 1008. Persistent storage 1008 may be a computer-readable medium on which are encoded instructions for carrying out operations of method 200 described above.

Communications unit 1010, in these illustrative examples, provides for communications with other data processing inspection systems or devices. In these illustrative examples, communications unit 1010 is a network interface card. Input/output unit 1012 allows for input and output of data with other devices that may be connected to system controller 130. For example, input/output unit 1012 may provide a connection for user input through a keyboard, a mouse, and/or some other suitable input device. Further, input/output unit 1012 may send output to a printer. Display 1014 provides a mechanism to display information to a user.

Instructions for the operating inspection system, applications, and/or programs may be located in storage devices 1016, which are in communication with processor unit 1004 through communications framework 1002. The processes of the different embodiments may be performed by processor unit 1004 using computer-implemented instructions, which may be located in a memory, such as memory 1006.

These instructions are referred to as program code, computer usable program code, or computer readable program code that may be read and executed by a processor in processor unit 1004. The program code in the different embodiments may be embodied on different physical or computer readable storage media, such as memory 1006 or persistent storage 1008.

Program code 1018 is located in a functional form on computer readable media 1020 that is selectively removable and may be loaded onto or transferred to system controller 130 for execution by processor unit 1004. Program code 1018 and computer readable media 1020 form computer program product 1022 in these illustrative examples. In one example, computer readable media 1020 may be computer readable storage media 1024 or computer readable signal media 1026.

In these illustrative examples, computer readable storage media 1024 is a physical or tangible storage device used to store program code 1018 rather than a medium that propagates or transmits program code 1018.

Alternatively, program code 1018 may be transferred to system controller 130 using computer readable signal media 1026. Computer readable signal media 1026 may be, for example, a propagated data signal containing program code 1018. For example, computer readable signal media 1026 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for system controller 130 are not meant to provide architectural limitations to the manner in which different embodiments may be implemented. The different illustrative embodiments may be implemented in a data processing inspection system including components in addition to and/or in place of those illustrated for system controller 130. Other components shown in FIG. 7 can be varied from the illustrative examples shown. The different embodiments may be implemented using any hardware device or inspection system capable of running program code 1018.

Examples of Aircraft and Methods of Fabricating and Operation Aircraft

Figure 8:
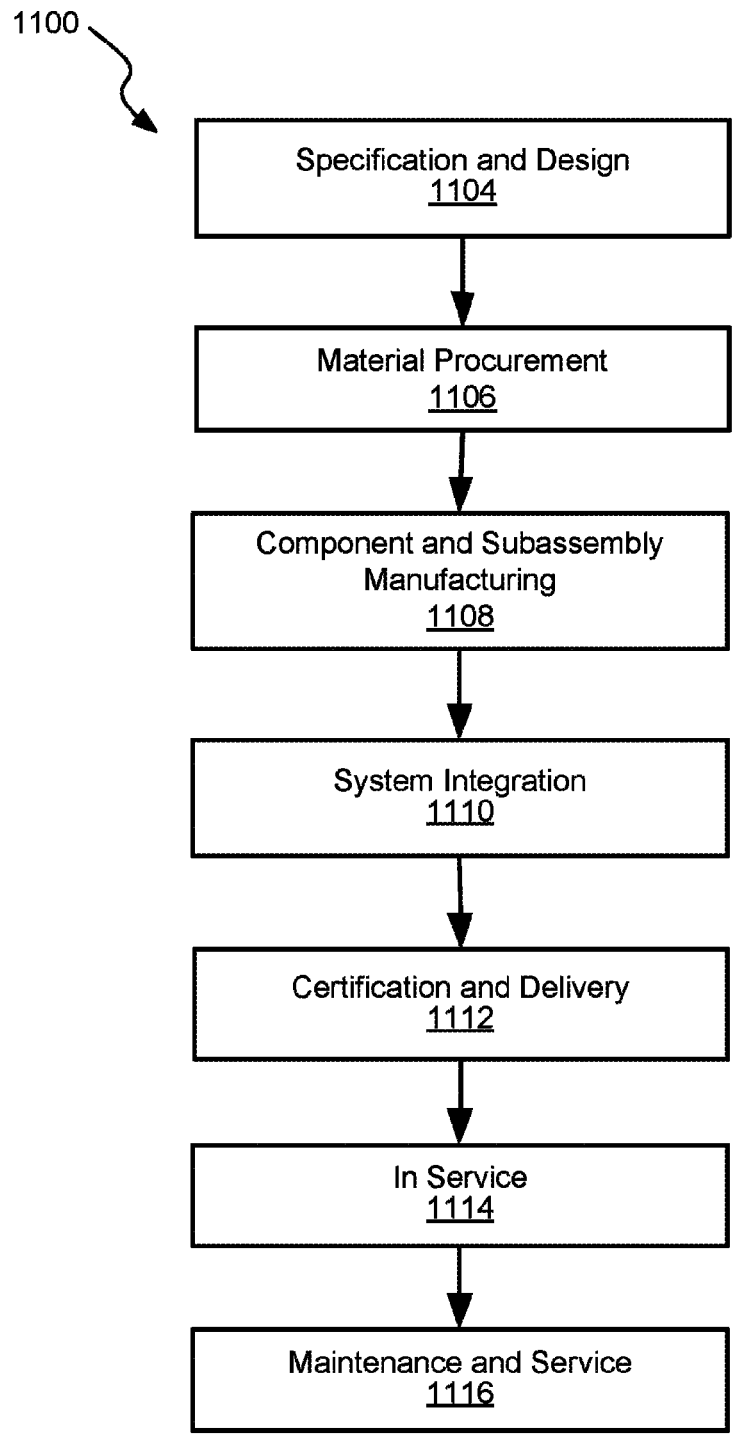
FIG. 8 is a block diagram of aircraft production and service methodology that may utilize methods and systems for evaluating height deviations on surfaces of composite structures described herein.
Figure 9:
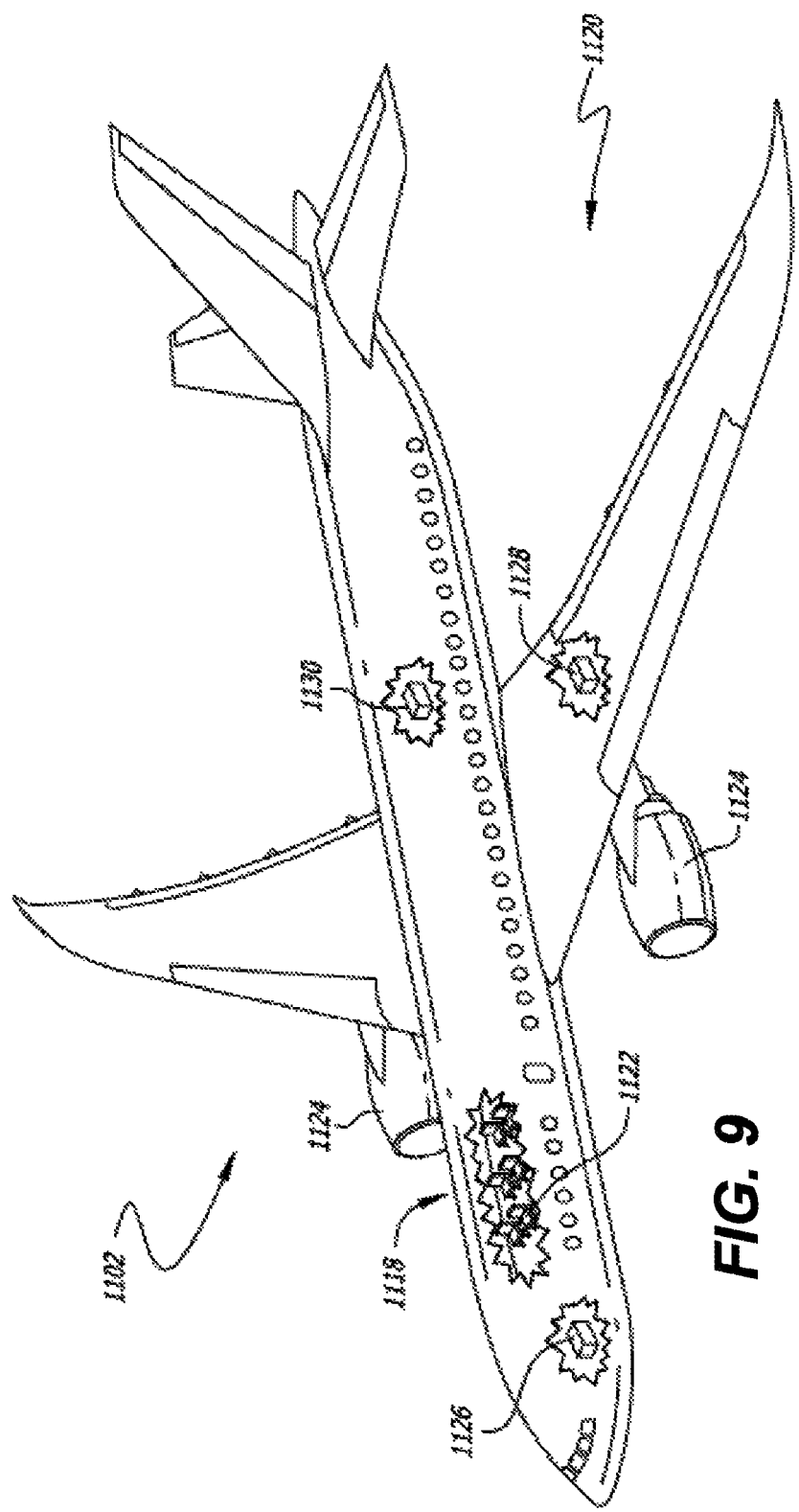
FIG. 9 is a schematic illustration of an aircraft that may include composite structures described herein.

Examples of the present disclosure may be described in the context of aircraft manufacturing and service method 1100 as shown in FIG. 8 and aircraft 1102 as shown in FIG. 9. During pre-production, illustrative method 1100 may include specification and design (block 1104) of aircraft 1102 and material procurement (block 1106). During production, component and subassembly manufacturing (block 1108) and inspection system integration (block 1110) of aircraft 1102 may take place. Methods of inspecting surfaces of components described above may be performed during one or more of these stages. Thereafter, aircraft 1102 may go through certification and delivery (block 1112) to be placed in service (block 1114). While in service, aircraft 1102 may be scheduled for routine maintenance and service (block 1116). Routine maintenance and service may include modification, reconfiguration, refurbishment, etc. of one or more inspection systems of aircraft 1102.

Each of the processes of illustrative method 1100 may be performed or carried out by an inspection system integrator, a third party, and/or an operator (e.g., a customer). For the purposes of this description, an inspection system integrator may include, without limitation, any number of aircraft manufacturers and major-inspection system subcontractors; a third party may include, without limitation, any number of vendors, subcontractors, and suppliers; and an operator may be an airline, leasing company, military entity, service organization, and so on. The described methods and systems be used on during specification and design (block 1104) of aircraft 1102 and component and subassembly manufacturing (block 1108). For example, various composite structures used for airframe and interior may be inspected (e.g. for height deviations) during process development and/or actual fabrication. Specifically, the described inspection methods and systems may be used firing component and subassembly manufacturing 1108, system integration 1110, and service 1114 of wing, fuselage, empennage, door, and nacelle of aircraft 1102.

As shown in FIG. 9, aircraft 1102 produced by illustrative method 1100 may include airframe 1118 with a plurality of high-level inspection systems 1120 and interior 1122, which may include the one or more flush mountable bottle openers. Examples of high-level inspection systems 1120 include one or more of propulsion inspection system 1124, electrical inspection system 1126, hydraulic inspection system 1128, and environmental inspection system 1130. Any number of other inspection systems may be included. Although an aerospace example is shown, the principles disclosed herein may be applied to other industries, such as the automotive industry. Accordingly, in addition to aircraft 1102, the principles disclosed herein may apply to other vehicles, e.g., land vehicles, marine vehicles, space vehicles, etc.

Apparatus(es) and method(s) shown or described herein may be employed during any one or more of the stages of manufacturing and service method (illustrative method 1100). For example, components or subassemblies corresponding to component and subassembly manufacturing (block 1108) may be fabricated or manufactured in a manner similar to components or subassemblies produced while aircraft 1102 is in service (block 1114). Also, one or more examples of the apparatus(es), method(s), or combination thereof may be utilized during production stages (bock 1108) and (block 1110), for example, by substantially expediting assembly of or reducing the cost of aircraft 1102. Similarly, one or more examples of the apparatus or method realizations, or a combination thereof, may be utilized, for example and without limitation, while aircraft 1102 is in service (block 1114) and/or during maintenance and service (block 1116).

Conclusion

Different examples of the apparatus(es) and method(s) disclosed herein include a variety of components, features, and functionalities. It should be understood that the various examples of the apparatus(es) and method(s) disclosed herein may include any of the components, features, and functionalities of any of the other examples of the apparatus(es) and method(s) disclosed herein in any combination, and all of such possibilities are intended to be within the spirit and scope of the present disclosure.

Many modifications of examples set forth herein will come to mind to one skilled in the art to which the present disclosure pertains having the benefit of the teachings presented in the foregoing descriptions and the associated drawings.

Therefore, it is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims. Accordingly, parenthetical reference numerals in the appended claims are presented for illustrative purposes only and are not intended to limit the scope of the claimed subject matter to the specific examples provided in the present disclosure.

What is claimed is:

1. A method of inspecting a surface of a component, the method comprising:
    aligning a first line scanner, which projects a first line of light, and a second line scanner, which projects a second line of light, relative to each other and to the surface of the component such that a first portion of the surface is illuminated by the first line of light in a first field of measurement and wherein a second portion of the surface is illuminated by the second line of light in a second field of measurement and wherein the first field of measurement and the second field of measurement overlay on a third portion of the surface;
    scanning the first portion of the surface using the first line of light from the first line scanner during a first time period in which the first line of light is turned on and off such that scanning the first portion produces a first data set corresponding to the first portion wherein the scanning includes capturing;
    scanning the second portion of the surface using the second line of light from the second line scanner during a second time period in which the second line of light is turned on and off wherein the second time period is offset relative to the first time period such that scanning the second portion produces a second data set corresponding to the second portion wherein the second time period is selected to reduce interference between the first line of light emitted from the first line scanner and the second line of light emitted from the second line scanner on the third portion of the surface where the first field of measurement and the second field of measurement overlap; and
    aggregating the first data set and the second data set into a combined data set.

2. The method of claim 1, wherein the first time period does not overlap with the second time period.

3. The method of claim 1, wherein the second time period starts immediately after the first time period.

4. The method of claim 1, wherein the first time period partially overlaps with the second time period.

5. The method of claim 1, wherein the first field of measurement of the first line scanner is co-linear with the second field of measurement of the second line scanner.

6. The method of claim 1, wherein the first portion of the surface is co-linear to the second portion of the surface.

7. The method of claim 1, wherein the first portion of the surface is parallel and offset with the second portion of the surface.

8. The method of claim 1, wherein the combined data set comprises a first non-overlapping portion of the first data set and a second non-overlapping portion of the second data set.

9. The method of claim 8, wherein the combined data set further comprises a combination of a first overlapping portion of the first data set and a second overlapping portion of the second data set.

10. The method of claim 9 wherein the combination of the first overlapping portion of the first data set and the second overlapping portion of the second data set is an average of the first overlapping portion of the first data set and the second overlapping portion of the second data set.

11. The method of claim 1, wherein aggregating the first data set and the second data set comprises spatially aligning the first data set and the second data set.

12. The method of claim 1, wherein spatially aligning the first data set and the second data set is performed based on aligning the first line scanner and the second line scanner relative to each other and to the surface of the component.

13. The method of claim 1, wherein the component changes position relative the first line scanner while scanning the second portion using the second line scanner.

14. The method of claim 13, wherein the component changes position relative to the first line scanner while scanning the first portion using the first line scanner.

15. The method of claim 14, wherein the component changes position relative to the first line scanner and relative to the second line scanner at the same time.

16. The method of claim 13, wherein the component changes position relative to the first line scanner in a direction perpendicular to the first field of measurement of the first line scanner.

17. The method of claim 13, further comprising scanning a fourth portion of the surface using the first line of light of emitted from the first line scanner during a third time period such that scanning the fourth portion produces a third data set corresponding to the fourth portion and that the third time period being offset relative to the first time period and being offset relative to the second time period.

18. The method of claim 1, further comprises scanning a fourth portion of the surface using third line of light emitted from a third line scanner during the first time period such that scanning the fourth portion produces a third data set corresponding to the fourth portion and such that a third field of measurement of the third line scanner partially overlaps with the second field of measurement of the second line scanner on a fifth portion of the surface, the third data set being aggregated together with the first data set and the second data set.

19. A method of aggregating data sets obtained from multiple line scanners used for inspecting a surface of a component, the method comprising:
    aligning the multiple line scanners in an array for a linear inspection of the surface wherein each of the multiple line scanners emit a line of light such that field of measurements of the lines of lights emitted from each pair of adjacent line scanners of the multiple line scanners overlap on a portion of the surface;
    scanning the surface using the multiple line scanners such that scanners in each pair of the adjacent line scanners operate at different time periods during which each of the multiple line scanners are turned on and off wherein the different time periods are selected to reduce interference between the lines of light emitted from each pair of the adjacent line scanners on the portion of the surface where the lines of lights overlap:
    aggregating the data sets produced by the multiple line scanners during scanning the surface into a combined data set.

20. An inspection system for inspecting a surface of a component, the system comprising:
    a first line scanner for scanning a first portion of the surface during a first time period and producing a first data set corresponding to the first portion wherein the scanning of the first line scanner includes illuminating the first portion with a first light and capturing a first optical image of the first portion of the surface:
    a second line scanner for scanning a second portion of the surface during a second time period offset relative to the first time period wherein the scanning of the second line scanner includes illuminating the second portion with a second light and capturing a second optical image of the second portion of the surface and producing a second data set corresponding to the second portion, wherein the first portion and the second portion overlap on a third portion of the surface and wherein the second time period is selected to reduce interference between first light and the second light on the third portion; and
    a system controller for aggregating the first data set and the second data set into a combined data set.

* * * * *